US010844339B2

(12) United States Patent
McKim

(10) Patent No.: US 10,844,339 B2
(45) Date of Patent: *Nov. 24, 2020

(54) DYNAMIC MULTI ORGAN PLATE

(71) Applicant: IONTOX, LLC, Kalamazoo, MI (US)

(72) Inventor: James McKim, Kalamazoo, MI (US)

(73) Assignee: IONTOX, LLC, Kalamazoo, MI (US)

( * ) Notice: Subject to any disclaimer, the term of this patent is extended or adjusted under 35 U.S.C. 154(b) by 437 days.

This patent is subject to a terminal disclaimer.

(21) Appl. No.: 15/481,354

(22) Filed: Apr. 6, 2017

(65) Prior Publication Data

US 2017/0211025 A1    Jul. 27, 2017

Related U.S. Application Data

(63) Continuation of application No. 14/222,581, filed on Mar. 21, 2014, now Pat. No. 9,631,167.

(51) Int. Cl.
| C12M 3/00 | (2006.01) |
| C12M 1/00 | (2006.01) |
| C12M 1/32 | (2006.01) |
| C12N 5/071 | (2010.01) |

(52) U.S. Cl.
CPC ............ *C12M 23/12* (2013.01); *C12M 21/08* (2013.01); *C12M 23/58* (2013.01); *C12M 29/00* (2013.01); *C12M 29/04* (2013.01); *C12N 5/0697* (2013.01)

(58) Field of Classification Search
CPC ...... C12M 21/08; C12M 23/12; C12M 23/16; C12M 23/40; C12M 25/14; B01L 3/563
See application file for complete search history.

(56) References Cited

U.S. PATENT DOCUMENTS

| 2011/0250585 A1* | 10/2011 | Ingber .................. C12N 5/0696 435/5 |
| 2012/0214189 A1* | 8/2012 | Shuler .................... C12M 23/16 435/29 |
| 2014/0030752 A1* | 1/2014 | Cuiffi ..................... C12M 23/44 435/29 |

FOREIGN PATENT DOCUMENTS

| WO | 2013086329 A1 | 6/2013 |
| WO | 2013086486 A1 | 6/2013 |

OTHER PUBLICATIONS

The Extended European Search Report issued in EP 15766028 dated Oct. 19, 2017—7 pages.

* cited by examiner

*Primary Examiner* — Nathan A Bowers
(74) *Attorney, Agent, or Firm* — Acuity Law Group, PC; Michael A. Whittaker

(57) ABSTRACT

Disclosed herein are dynamic multi-organ plates comprising two or more wells, wherein the wells are configured for cell or tissue culture growth; at least one transwell tube in fluid communication with the two or more wells; and a pump in fluid communication with the at least one transwell tube.

11 Claims, 4 Drawing Sheets

US 10,844,339 B2

DYNAMIC MULTI ORGAN PLATE

CROSS-REFERENCE TO RELATED APPLICATIONS

The present invention is a continuation of U.S. patent application Ser. No. 14/222,581, filed Mar. 24, 2014, now U.S. Pat. No. 9,631,167, which is hereby incorporated in its entirety including all tables, figures and claims

FIELD OF THE INVENTION

The present invention is in the field of conducting bioanalytical assays, and more specifically, in the field of multi-organ assays

BACKGROUND OF THE DISCLOSURE

There is a growing need in the chemical, cosmetic, and pharmaceutical industries to understand and predict potential adverse effects of chemicals in humans without the use of animal experimentation. In particular, there is a significant need to predict repeat dose systemic toxicity or efficacy using cell cultures, as opposed to studying these effects in animal or human models. To date attempts have been made using single cell models that mimic specific organs. Biomedical engineering has begun to explore and develop the idea of incorporating organs onto microchips and has focused primarily on the micro environment and three dimensional components of each tissue. These technologies do not address mass to volume ratios of tissues to blood, nor do they provide a platform that enables bioanalytical evaluation of chemical effect. In addition, these early attempts have not incorporated a fluid dynamic system on a meso scale that will allow fluid communication between tissue compartments without fully exchanging compartment culture medium. Therefore, there is a real need for a tool that will allow scientists to incorporate existing technologies in their laboratories with a novel cell culture plate that will enable the evaluation of chemical safety in many human organs simultaneously.

SUMMARY OF THE INVENTION

Disclosed herein are dynamic multi-organ plates comprising two or more wells, wherein the wells are configured for cell or tissue culture growth; at least one transwell tube in fluid communication with the two or more wells; and a pump in fluid communication with the at least one transwell tube.

BRIEF DESCRIPTION OF THE DRAWINGS

FIG. 3A is a top view drawing showing an embodiment of a multi-walled well, while

DETAILED DESCRIPTION OF THE EMBODIMENTS

Figure 1A:
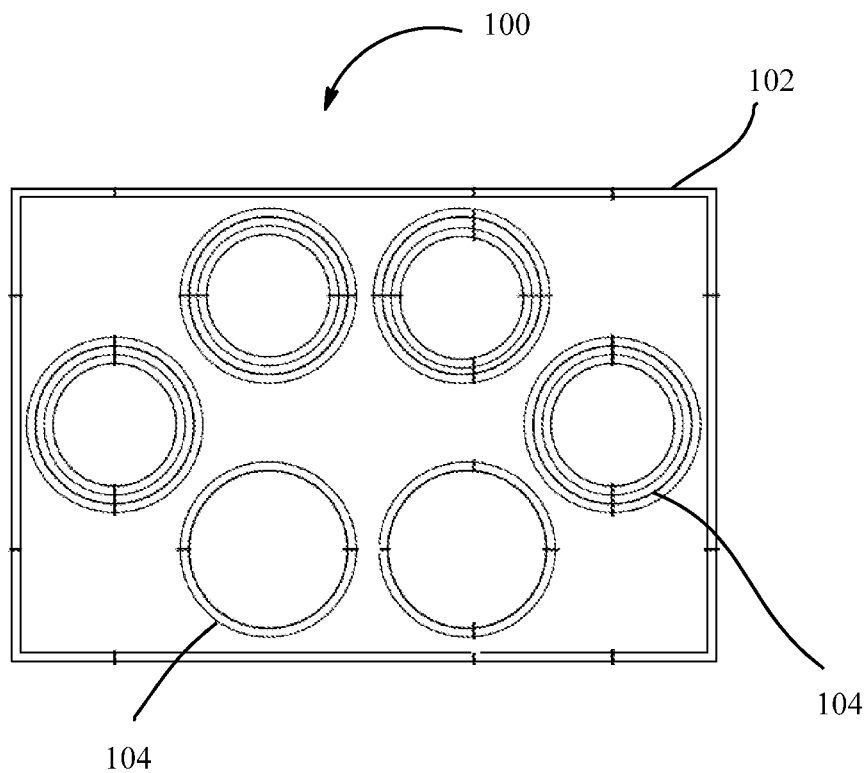
FIG. 1A is a top view drawing showing a 6 well layout of an embodiment of the disclosed dynamic multi organ plate (DMOP).

Disclosed herein are dynamic multi-organ plates (DMOP), which incorporate multiple tissue (organ) types with a mesoscale fluidic system. The large scale format of the disclosed DMOPs enables researchers to match tissue mass to blood volume by adjusting the surface area of the artificial semipermeable vessel system. These plates provide for the study of drug or chemical effects on multiple organs represented by cell or tissue culture in a single plate connected by a fluidic system that allows for analyte transfer without volume exchange between the wells. In certain configurations, organ simulation is improved by providing a vapor generation system over lung tissue and a mico electrode array to monitor human or animal cardiomyocyte beat activity.

In some aspects, the presently disclosed DMOP comprises multiple wells. Each well comprises cells or tissue from a single organ. The wells of the DMOP are in fluid communication with each other, either in parallel, or in series, or a combination of the two. A fluid, for example blood or a blood simulator, or any other fluid capable of carrying nutrients, or biological matter, flows into the DMOP and then from one well to another. Culture media in each well is isolated from the culture media of other wells. In certain embodiments, only biological materials and test materials and their metabolites can move between wells.

Currently available technologies do not provide a platform that enables bioanalytical evaluation of chemical effect. This is because the biological material being released or produced by a cell upon exposure to a test drug or chemical is not produced at a high enough concentration to allow detection. Furthermore, because cells from different tissues (e.g. liver or heart) require growth media with different components for optimal growth, an open exchange of media between wells can significantly disrupt cell growth. To address this issue, in some embodiments of the disclosed DMOPs, the fluid simulating blood flow is pumped through tubing having gaps of dialysis membrane. The membrane allows only analytes of interest to pass into and out off the simulated blood, thereby exposing all simulated organs in a manner similar to human blood flow. Because the order in which simulated blood flow reaches specific organs mimics human circulation, some embodiments of the disclosed DMOPs have a plate design with a well layout that facilitates this chemical exchange.

In some embodiments, the user of the disclosed DMOPs can combine pharmacokinetic modeling approaches, and thereby determine kinetic parameters such as metabolism, hepatic clearance, metabolic stability, protein binding, plasma vs time concentration curves, half-life, $C_{max}$, area under the curve, and even $IC_{50}$ values for specific transporters. The result is an integrated biological system that can be used to estimate systemic organ effects.

In some embodiments, the tissue culture in the wells grows two-dimensionally, while in other embodiments, the tissue culture grows three-dimensionally. The isolation of the culture media between the wells allows for different supplements and culture media to be supplied to each well, depending on the type of cell or tissue being cultured, and depending on whether the growth is a 2D or 3D culture.

In some embodiments, the wells of the disclosed DMOPs are connected to each other using transwell tubes, i.e., tubes that connect one well to another. In some embodiments, a single transwell tube connects two wells. In another embodiment, a transwell tube imports fluid into a well while another transwell tube carries fluid away from the well. This combination mimics the artery/vein system in an organism.

In some embodiments the transwell tubes are prefabricated into the DMOP. In other embodiments, the user can arrange the wells as the user desires, and then insert the transwell tubes in the desired manner to connect the wells.

In some embodiments, the cells are grown on transwell membranes in the well that effectively allows cells to form an apical (top) and basolateral (lower) chamber. Simulated blood flow moves under the transwell in the growth medium just as blood would move. Cells containing uptake and efflux transporters (e.g. OATP1B1 and BSEP) orientate to the basolateral or apical sides of the cell (polarization). Tubing and dialysis membranes in each well provide a one-way flow of fluids or nutrients across the transwell tube wall. Thus, the tube simulating blood flow is below the basolateral side of the transwell tube.

In some embodiments, a dialysis membrane separates the inlet and outlet sides of the tubing in the wells and the transwell tubes. This membrane provides for an effective communication between wells. The fluid carrying osmotically active components such as drugs, drug metabolites or biological components such as glucose, cytokines, growth factors, and the like, can move down a concentration gradient by passive diffusion into the well from the tubing or into the tubing from the cell. There is no net change in volume so the cell culture wells remain unique in their individual properties. The simulated vasculature only exchanges low molecular weight components not present in wells through the membrane. In some embodiments, the components include test chemicals, their metabolites, cell/tissue products, and even small proteins.

The tissues in the wells can be placed such that the fluid passes through them in the same order as it would inside of an organism. For example, the fluid can pass through a well having gastrointestinal tissue/cells, before it reaches a well having liver tissue/cells, and then moving on to a well having lung tissue/cells. In this sense, the DMOP simulates a multi-organ organism having multiple tissue types that are in fluid communication with each other. Markers of cell health can be collected in the perfusate running through the tube system or directly from the wells. The DMOP, then, allows for testing of compounds or biologically active materials in a multi-organ system without the need to conduct animal testing.

Herein, the word "plate" is used interchangeably with "dynamic multi-organ plate" and with "DMOP."

In some embodiments, the DMOP is constructed of a material, for example plastic, that is compatible with cell culture. By "compatible with cell culture" it is meant that the composition of the plate does not adversely interfere with the function of the tissue or with the function of any test compounds. In other words, a material that is compatible with cell culture is considered to be a biologically inert material.

In some embodiments, the plate comprises large wells, which are at least 0.5 inch in diameter. In certain embodiments, the wells have diameters of 1 inch, and in other embodiments, the diameter is greater than 1 inch, for example 1.25", 1.5", 1.75", 2", 2.25", 2.5", 2.75", 3", and the like.

In some embodiments the plate comprises at least two wells. In certain embodiments, the plate comprises 4, 6, 8, or 10 wells. In some embodiments, the plate comprises more than 10 wells. In other embodiments, the plate comprises an odd number of wells, for example 3, 5, 7, 9, etc., wells.

In some embodiments, the wells are connected by inserted tubing and dialysis membrane. In other embodiments, the wells are linked by channels within the walls of the wells. In some embodiments, the channels are open channels, i.e., channels whose top is open to the outside and form a generally half-pipe shape. In other embodiments, the channels are closed channels, i.e., tubes formed within the walls of the wells, connecting two adjoining wells.

Figure 1B:
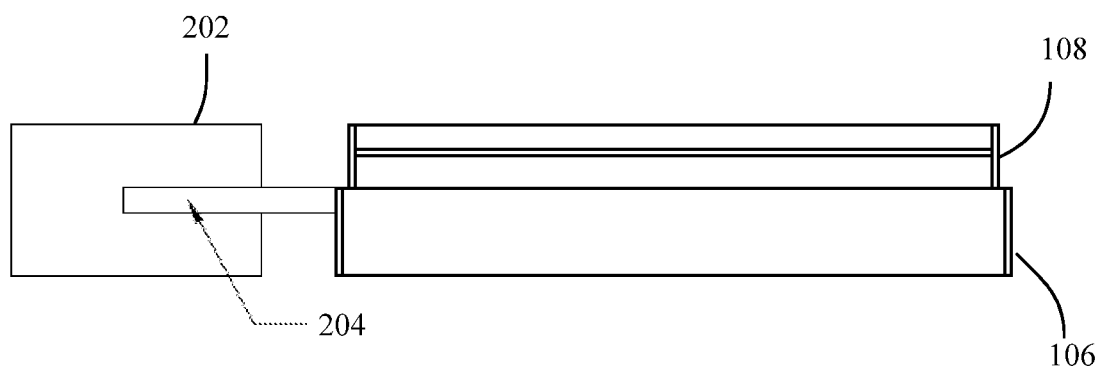
FIG. 1B is a side view of an embodiment of the disclosed DMOP demonstrating a foot print of the plate.

FIG. 1A shows an embodiment of a DMOP 100. The DMOP 100 comprises a body 102 that contains the various components. In this embodiment, the DMOP 100 comprises six wells 104. The wells 104 can be arranged in any order that best accommodates the needs of the experiment. For example, in some embodiments, the wells 104 are arranged in a line to facilitate a fluidic connection in series. In other embodiments, for example the embodiment shown in FIG. 1, the wells 104 are arranged in a hexagon format that can facilitate a fluidic connection between all the plates simultaneously. Other arrangements that mimic well-defined geometric shapes, or random arrangements are also contemplated. In some embodiments, the mesoscale format has a standard cell culture foot print that allows the plate to be analyzed by current commercially available plate readers or to be manipulated in standard robotic platforms. FIG. 1B shows the side view of one embodiment of DMOP 100 and its footprint. In the illustrated embodiment, the DMOP body 102 has two sections. A lower section 106 contains the wells 104. Thus, in this embodiment, the height of the section 106 is equivalent to the height of the wells 104. An upper section 108 provides additional containment to avoid spillage, either into the device or out of the device. FIG. 1B shows the location of an inlet pipe 204 and a pump 202, as described fully below.

In some embodiments, the plate is configured to accommodate tissue from an organism in its wells. In certain embodiments, the various tissues used in the wells are all from the same species. In other embodiments, tissue from different species is used in different wells. In certain embodiments, the organism is an animal. In some of these embodiments, the animal is a vertebrate. In certain embodiments, the organism is a mammal. In some embodiments, the mammal is selected from the group consisting of mice, rats, rabbits, guinea pigs, dogs, cats, sheep, goats, cows, primates, such as monkeys, chimpanzees, and apes, and humans. Fish cells or whole fish such as the zebra fish may also be used in these wells.

In some embodiments, the tissue comprises cells derived from stem cells. In other embodiments, the tissue comprises mature cell lines. In some embodiments, the tissue, for example primary or cyropresesrved hepatocytes in sandwich culture, is grown within each well. In other embodiments, the tissue is grown elsewhere and then transferred into the DMOP's well for analysis. In yet other embodiments, the tissue is grown within the well elsewhere, and then the well is inserted into the plate for the analysis.

Because the system allows for a larger mass of cells to be grown, it is possible to measure standard biochemical and molecular endpoints that can be used to determine chemical or drug effects on the cells. In some embodiments, the plate is organized in a manner that mimics human tissue placement and blood flow.

Figure 2:
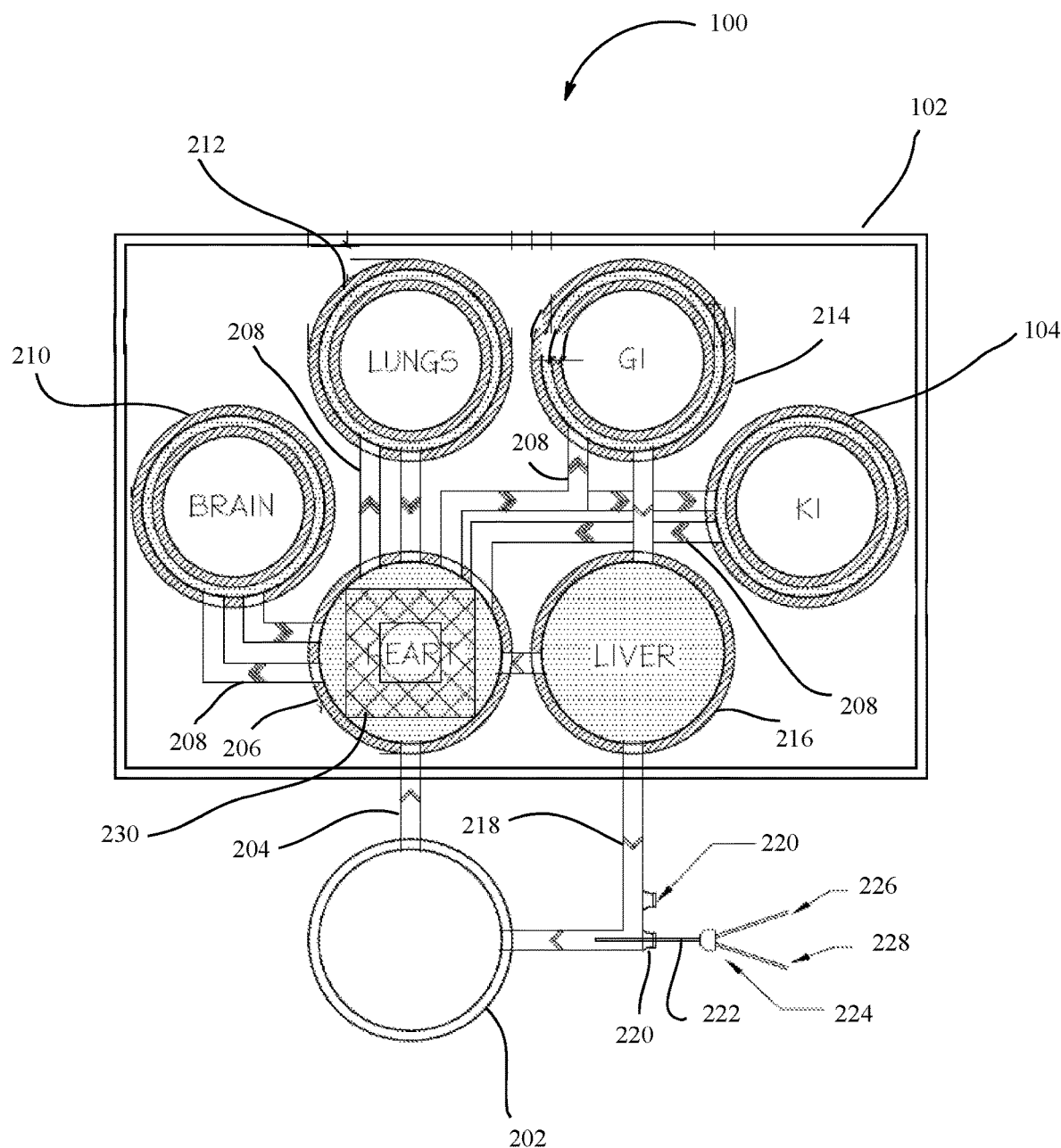
FIG. 2 is a top view of an embodiment of the disclosed DMOP showing organ placement and simulated blood flow.

FIG. 2 shows one embodiment of the DMOP 100, in which the wells 104 are in fluid communication with each other. All the internal components, i.e., the wells 104 and the pipes 208 (see below) are contained within the plate body 102. In this embodiment, a peristaltic pump 202, located outside of the body 102, is provided that pumps fluid, for example water, saline, blood or a simulated blood, into the system through an inlet pipe 204. In this embodiment, the fluid enters a first well 206 having heart tissue. From this well 206, the fluid travels through pipes 208 to a well 210 having brain tissue grown on a transwell plateform to mimic the blood brain barrier. Because in humans blood travels from the heart to the brain and then from the brain returns to the heart, in the illustrated DMOP a transwell pipe 208 returns the fluid from the brain well 210 back to the heart well 206. This is also true of the well 212 having lung tissue. The fluid flow from the heart well 206 to the lung well 212 is bidirectional, i.e., the fluid travels from the heart well 206 to the lung well 212 and then returns to the heart well 206. Further, in a human blood flow to the lungs and the brain are independent of each other. Similarly, in the illustrated DMOP, fluid flow to the lung well 212 and the brain well 210 are carried out by independent pipes 208.

However, the situation with certain organs, for example the gastrointestinal (GI) tissue and liver tissue is different. In a human, the blood flows from the heart to the GI system, and during first pass, goes from the GI system to the liver, and from the liver returns to the heart. Similarly, in the illustrated DMOP, fluid flows unidirectionally from the heart well 206 to the GI well 214, then to the liver well 216, and then back to the heart well 206. Thus, the transwell pipes 208 between the heart well 206, the GI well 214, and the liver well 216 allow tissues with polarity (i.e., those tissues that function under a unidirectional fluid flow, e.g. GI tract cells, lung cells, and kidney cells) to be cultured in a way that allows the functionality of transporters to be assessed.

The embodiment of FIG. 2 shows both bidirectional and unidirectional fluid flow from one well to another. In some embodiments, all wells are under a bidirectional flow, whereas in other embodiments, all wells are under a unidirectional flow. In some embodiments, the transwell pipes 208 are inserts that the operator can introduce. Thus, in these embodiments, the DMOP is modular where the operator chooses the number and/or location of the wells on the plate and then, by placing the transwell pipe inserts, determines the flow of fluid from one well to another.

The fluid exits the plate body 102 through one of the wells. In the illustrated embodiment, the fluid exits the liver well 216 through the outlet pipe 218, which reconnects with the peristaltic or microsyringe pump 202. In some embodiments, a well port 220 is provided. Some embodiments of the disclosed DMOP comprise more than one well port 220. For example, the embodiment illustrated in FIG. 2 comprises two well ports 220. While in the illustrated embodiment the well port 220 is on the outlet pipe 218, the skilled artisan recognizes that the port 220 can be placed anywhere on the system that is convenient to reach. For example the port 220 can be placed on the inlet pipe 204, or on one of the transwell pipes 208. The open end of the well port 220 is configured to allow exogenous substances to be introduced into the system. In some embodiments, the open end of the well port 220 comprises a rubber stopper or septum, or similar material. Exogenous substances can then be injected into the fluid of the system using a syringe. In some embodiments, a hose or pipe can be connected to the well port 220, which hose/pipe is connected to a reservoir comprising the exogenous substance at the other end such as a bioreactor unit to increase metabolites. In some embodiments, a pump is used to introduce the exogenous substance into the system.

In some embodiments, an input/output line 222 is inserted into a well port 220. In certain of these embodiments, the input/output line 222 comprises a junction 224 that controls the flow either into the system, through an inlet hose 226, or out of the system, through an outlet hose 228. In some embodiments, the junction 224 is a 3-way valve. In other embodiments, the junction 224 is simply a rubber septum, into which the inlet hose 226 and the outlet hose 228 are inserted. Through this system, an exogenous substance can be introduce into the system through the inlet hose 226 and aliquots of the internal fluid can be taken out through the outlet hose 228.

In some embodiments, the exogenous substance is a drug, protein, or other chemical that is under study.

In some embodiments, the system incorporates microarray electrode technology in order to monitor the effect of an exogenous chemical or drug on heart beat. In these embodiments, the microarray 230 is placed in the heart well 206. These electrodes measure the electrocardiogram of the heart tissue in the heart well 206. In some embodiments, holes are placed in the inserted MEA well to allow for simulated blood/fluid flow. In some of these embodiments, the system is started and the beat of the heart tissue is measured. The exogenous substance is then introduced through the well port 218. The beat of the heart tissue is then measured again, and the effect of the exogenous substance is determined.

In some embodiments, aliquots of the fluid within the system is extracted through the well port 218 for chemical analysis, for example gas chromatography (GC), liquid chromatography/mass spectrometry (LC-MS), high pressure liquid chromatography (HPLC), and the like. The analysis can provide a real time measurement of, for example, metabolite formation, tissue damage, rate of diffusion into tissues, and other pharmacological and biochemical parameters.

Figure 3A:
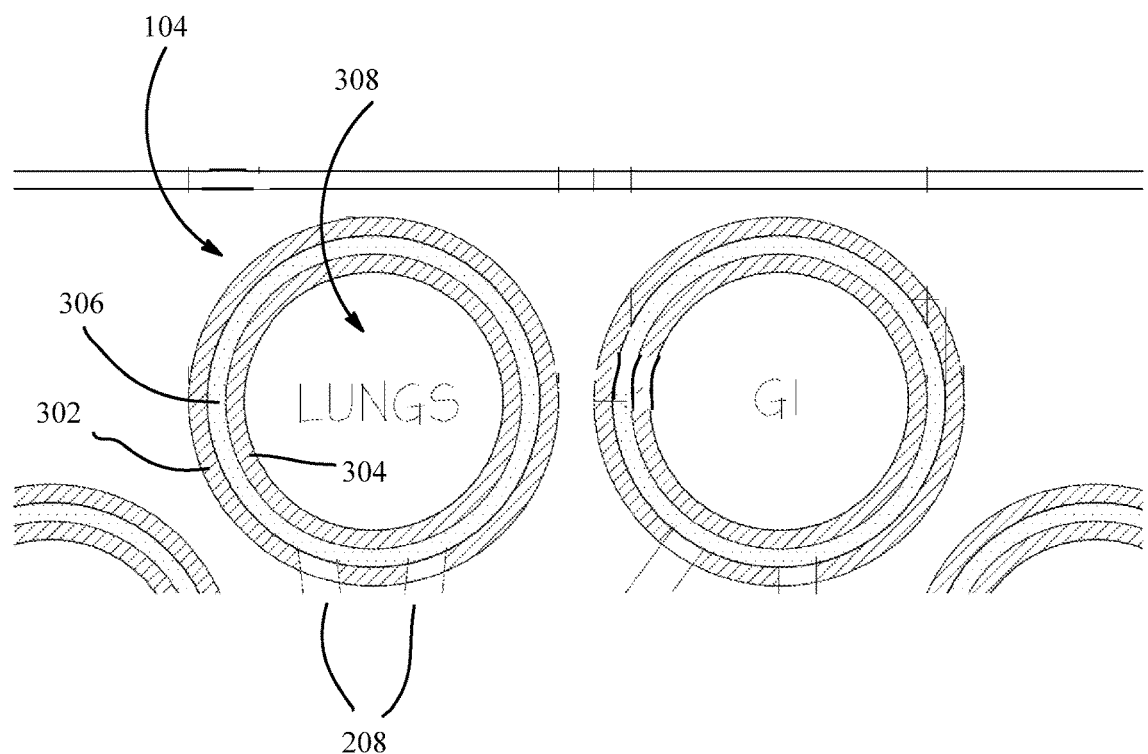

FIG. 3A shows a close-up top view of an embodiment of the wells 104. The wells 104 comprise an outer shell 302 (outer hatched space), and insert 304 (inner hatched space), and a fluid space 306 (dotted space). In some embodiments, the outer shell 302 is a solid piece and defines the shape of the well 104. The insert 304 comprises a semipermeable wall that allows for diffusion of chemicals, gasses, and fluids between the fluid space 306 and the interior 308 of the well 104. The fluid space 306 is in fluid communication with the transwell pipes 208 (e.g. the dialysis membrane between the inlet and outlet tubes allows for diffusion into the culture wells). Diffusion through the semipermeable barrier 304 mimics the diffusion of gasses and chemicals between the capillaries and the cells of a tissue in a human.

Figure 3B:
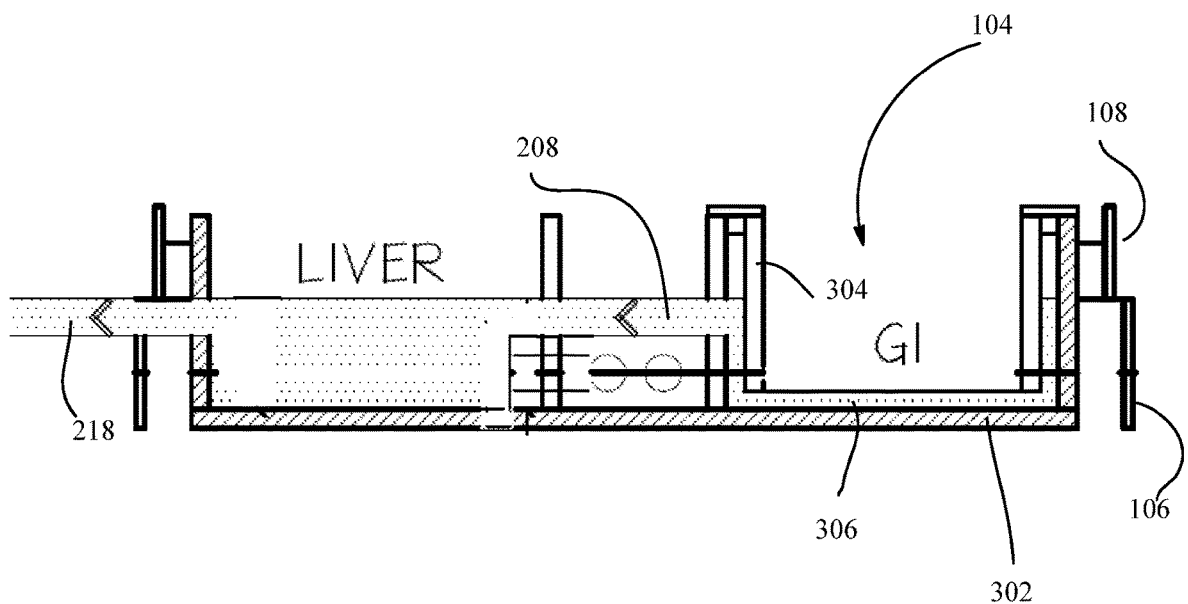
FIG. 3B is a side view drawing showing the same.

FIG. 3B shows a side view of the wells 104 within an embodiment of the disclosed DMOP. The flow of the fluid under and around the insert 304 in the fluid space 306 is clearly shown. In some embodiments, the amount of fluid in the system is increased to manipulate the simulated blood volume and surface area. In some of these embodiments, the fluid space 306 becomes larger as more fluid is introduced in the system, while the insert 304 shrinks. Thus, increasing the amount of fluid in the system results in a lower contact surface area between the tissue and the fluid and vice versa. This closely mimics actual physiological conditions. By varying the dialysis area in the well between the inlet and outlet tubing it is possible to change the fluid to mass ratio and simulate organs with different degrees of blood perfusion.

In some embodiments, in order to develop a more accurate lung chamber reconstructed human lung tissue (such as one developed by Epithelix, (Geneva Switzerland)) can be used to mimic human lung. This tissue is grown at an air liquid interface, which allows for the exposure of vapors, and aerosols to the lung and subsequent transfer into blood. In some embodiments, the lung well is fitted with a hollow chamber that mimics an inhalation chamber. The use of an inhalation chamber allows an operator to develop inhalation exposure and toxicity models.

Figure 4:
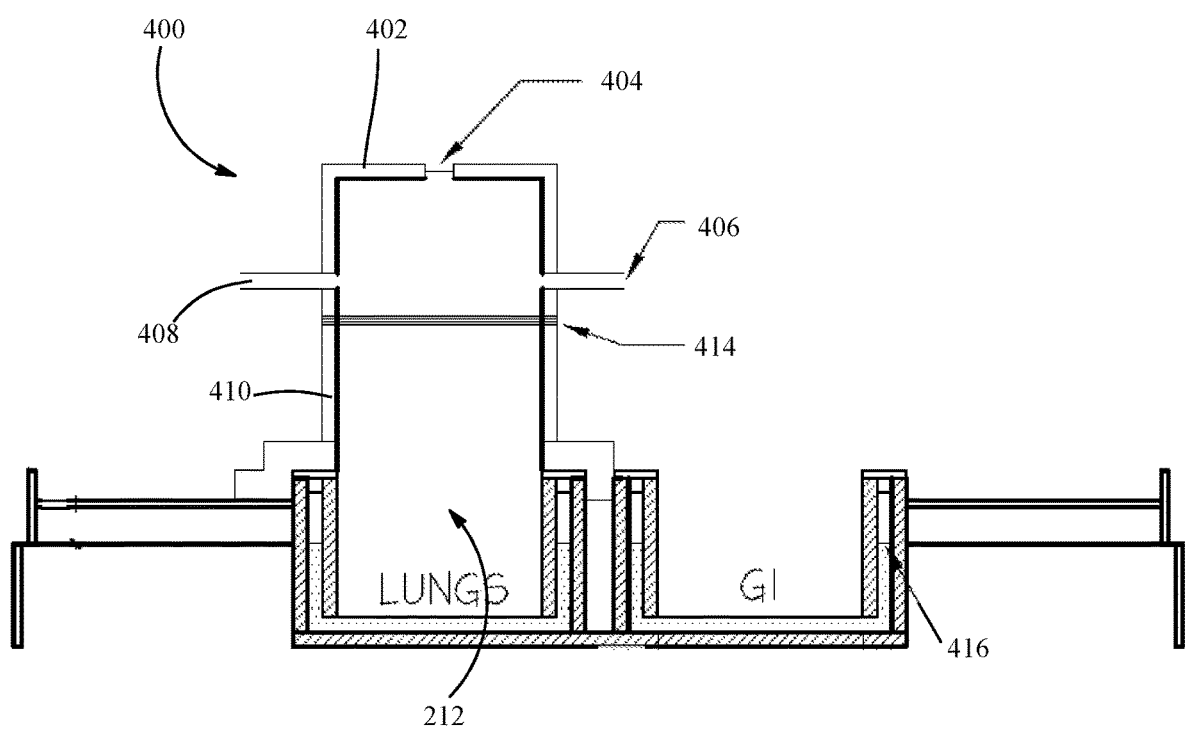
FIG. 4 is a drawing showing a lung well with an inhalation chamber.

FIG. 4 shows an embodiment of the chamber 400, which is fitted over the lung well 212. The chamber 400 comprises a body 402. In some embodiments, an opening 404 is provided to allow the operator to introduce fluids or other substances into the chamber. In some embodiments, the opening 404 is sealed by a rubber stopper or septum, and the like.

In some embodiments, the chamber 400 is linked to a vapor generator, such as a J tube. The vapor generator (not shown) is connected to the chamber by an inlet port 406. The gasses exit the chamber through an outlet port 408. In some embodiments, the chamber 400 comprises two separate pieces. A lower piece 410 is configured to fit over the lung well 212, while the upper piece 412 features the inlet port 406 and the outlet port 408. In some embodiments, an o-ring seal 414 provides a gas-tight seal between the two pieces. Line 416, and the corresponding line in all the figures, when applicable, shows the liquid line in the system.

What is claimed is:

1. A plate comprising,
    at least one well configured for lung cells or lung tissue culture growth, the well comprising a hollow chamber located over the well;
    the hollow chamber comprising a sealable opening, an inlet port, and an outlet port;
    at least one transwell tube in fluid communication with the inlet port; and
    the opening configured to allow the introduction of substances to the well; and
    a pump in fluid communication with the at least one transwell tube;
    wherein the well comprises an outer shell and an insert, wherein the insert is semipermeable,
    wherein the insert forms a hollow interior, into which lung cells or lung tissue culture is placed;
    wherein the insert allows for diffusion of chemicals, gasses, and fluids between the interior of the well and a space for fluid between the outer shell and the insert;
    wherein as more fluid is introduced into the plate, the fluid space becomes larger while the insert shrinks;
    wherein the fluid in the well is in contact with at least a portion of the insert;
    wherein the hollow interior of the insert is not in direct fluid communication with a transwell tube; and
    wherein the cells or tissue culture within the well is in fluid contact with fluid within the insert and in gaseous contact with the gasses in the hollow chamber.

2. The plate of claim 1, wherein the hollow chamber comprises a lower piece and an upper piece.

3. The plate of claim 2, wherein the lower piece is configured to fit over the lung well.

4. The plate of claim 2, wherein the upper piece comprises the inlet port and the outlet port.

5. The plate of claim 1, wherein the inlet port is in gaseous communication with a vapor generator.

6. The plate of claim 2, further comprising a gas-tight seal between the lower piece and the upper piece.

7. The plate of claim 1, wherein the at least one transwell tube comprises a polarized wall which provides a one-way flow of fluids or nutrients across the polarized wall.

8. The plate of claim 1, wherein the at least one transwell tube comprises a well port, through which a substance is introduced into a lumen of the at least one transwell tube, or through which an aliquot of fluid within a lumen of the at least one transwell tube is removed.

9. The plate of claim 8, wherein the substance is a small organic molecule or a protein.

10. The plate of claim 1, wherein the fluid space is in fluid communication with the at least one transwell tube.

11. A method of growing cells or tissue culture in a dynamic multi-organ plate, the method comprising:
    providing a dynamic multi-organ plate, wherein the plate comprises
        two or more wells, wherein the wells are configured for cell or tissue culture growth;
        at least one transwell tube in fluid communication with the two or more wells; and
        a pump in fluid communication with the at least one transwell tube;
        wherein the well comprises an outer shell and an insert, wherein the insert is semipermeable,
        wherein the insert forms a hollow interior, into which lung cells or lung tissue culture is placed;
        wherein the insert allows for diffusion of chemicals, gasses, and fluids between the the interior of the well and a space for fluid between the outer shell and the insert;
        wherein as more fluid is introduced into the plate, the fluid space becomes larger while the insert shrinks;
        wherein the fluid in the well is in contact with at least a portion of the insert; and
        wherein the hollow interior of each insert is not in direct fluid communication with a transwell tube;
    placing the cells or tissue culture to be grown in a well of the plate; and
    introducing a fluid into the transwell tube.

* * * * *